United States Patent [19]

Provost et al.

[11] 4,164,566
[45] Aug. 14, 1979

[54] HEPATITIS A VIRUS CELL CULTURE IN VITRO

[75] Inventors: Philip J. Provost, Harleysville; Maurice R. Hilleman, Lafayette Hill, both of Pa.

[73] Assignee: Merck & Co., Inc., Rahway, N.J.

[21] Appl. No.: 934,293

[22] Filed: Aug. 17, 1978

[51] Int. Cl.$^2$ .................. A61K 39/12; C12K 7/00
[52] U.S. Cl. ................................ 424/89; 195/1.3
[58] Field of Search ..................... 195/1.3; 424/89

[56] References Cited

U.S. PATENT DOCUMENTS

| 3,935,066 | 1/1976 | Apostolov | 195/1.7 |
| 4,029,764 | 6/1977 | Provost et al. | 424/89 |
| 4,031,203 | 6/1977 | Provost et al. | 424/89 |

OTHER PUBLICATIONS

Rightsel et al., Science, vol. 124, (1956), pp. 226–228.
O'Malley et al. – Proc. Exp. Biol. Med., vol. 108, (1961), pp. 200–205.
Liebhaber et al.–J. Exp. Med., vol. 122, (1965), pp. 1135–1150.
O'Malley et al.–Proc. Nat. Acad. Sci., vol. 56, (1965), pp. 895–901.
Mirkovic et al.–Proc. Soc. Exp. Biol. Med., vol. 138, (1971), pp. 626–631.
Dienstag et al.–Intervirology, vol. 6, (1975/1976), pp. 319–324.
Advances in Viral Hepatitis, W.H.O. Technical Report Series, (1977), pp. 15 & 61.

*Primary Examiner*—Sam Rosen
*Attorney, Agent, or Firm*—Donald J. Perrella; Julian S. Levitt

[57] ABSTRACT

Hepatitis A virus is passaged at least once in a susceptible sub-human primate; the infected liver from such passage is used to inoculate an in vitro cell culture, the inoculated cell culture is incubated until hepatitis A antigen is detected in the cell sheet or culture fluid, and at least two serial in vitro passages in cell culture are carried out. The hepatitis A virus so modified can be used to prepare live, attenuated hepatitis A vaccine or an inactivated hepatitis A vaccine.

9 Claims, No Drawings

HEPATITIS A VIRUS CELL CULTURE IN VITRO

BACKGROUND OF THE INVENTION

The present invention relates to hepatitis A virus and, more particularly, for a method for growing hepatitis A virus in cell culture.

Prior art attempts to propagate hepatitis A virus in cell culture uniformly have been unsuccessful. The inability to propagate the virus in cell culture has necessitated the use of susceptible sub-human primates to grow the virus so as to obtain antigen for diagnostic and therapeutic purposes. The scarcity and cost of most susceptible sub-human primates, however, renders such methods impractical for commercial use. The ability to propagate hepatitis A virus in cell culture would offer a signficant and outstanding achievement in this field.

OBJECTS OF THE INVENTION

It is, accordingly, an object of the present invention to provide a method for growing hepatitis A virus in cell culture. Another object is to provide conditions for the successful cell culture propagation of hepatitis A virus. These and other objects of the present invention will be apparent from the following description.

SUMMARY OF THE INVENTION

Hepatitis A virus is passaged at least once in a susceptible sub-human primate; the infected liver from such passage is used to inoculate an in vitro cell culture, the inoculated cell culture is incubated until hepatitis A antigen is detected in the cell sheet or culture fluid, and at least two serial in vitro passages in cell culture are carried out. The hepatitis A virus so modified can be used to prepare live, attenuated hepatitis A vaccine or an inactivated hepatitis A vaccine.

DETAILED DESCRIPTION

It has now been found that hepatitis A virus which has been adapted by at least one passage in the liver of a susceptible sub-human primate, e.g., marmoset, owl monkey, African green monkey, rhesus monkey, or chimpanzee, can be successfully passaged in cell culture. Preferably, there are at least 5 passages in the susceptible sub-human primate. It is also preferred that at least 2 sub-human primate species be used, and that there be at least 2 passages in each species.

Following the final passage, the infected liver is removed, homogenized and clarified and used to inoculate cell cultures.

The cell cultures may be primary marmoset liver cell cultures, primary African green monkey kidney cell cultures, primary rhesus monkey kidney cell cultures, primary cynomolgus monkey kidney cell cultures, fetal rhesus monkey kidney cell cultures, fetal cercopithecus monkey kidney cell cultures, fetal rufiventer marmoset kidney cell cultures, or any primary, continuous, or transformed kidney or liver cell culture derived from a human or sub-human primate susceptible to hepatitis A virus infection. The cell cultures may also consist of primary whole chick embryo or duck embryo cells or cells derived from the kidneys of newborn chicks or ducks.

The cell culture is incubated at from about 33° to about 39° C., preferably at from about 35° C. to about 37° C., until hepatitis A antigen can be detected either in the cell sheet or in the tissue culture fluid. Typically from about 7 to about 35 days are required for development of detectable hepatitis A antigen. The antigen is conveniently detected in the cell sheet by fluorescence antibody methods, and in the cell culture fluid either by immune adherence hemagglutination assay or by radioimmune assay.

Serial in vitro passages may be carried out indefinitely. With succeeding passages there is better adaptation of the virus to in vitro growth as evidenced by more rapid appearance of hepatitis A antigen and the production of larger quantities of the viral antigen.

After 5 or more serial in vitro passages of hepatitis A virus in the above cell types it is found that the virus is so modified as to enable ready cultivation in additional cell types as follows: human fetal diploid lung fibroblast cells, fetal rhesus diploid lung cells and fetal cercopithecus diploid lung cells. These cell types are all suitable for use in the preparation of live, attenuated human viral vaccines.

The human hepatitis A virus may be so modified by serial passages in the livers of sub-human primates and subsequent serial in vitro passages in cell cultures as to provide a live, attenuated human viral vaccine and additionally may be economically grown in such large quantity in cell culture as to enable production of sufficient viral antigen for preparation of an antigenic, immunogenic viral vaccine and also for the preparation of hepatitis A antigen for diagnostic purposes.

The hepatitis A antigen can be inactivated for use as a vaccine against hepatitis A virus. Inactivation of infectivity may be achieved by treatment with formalin. The amount of formalin employed is effective to inactivate the infectivity of the antigen while retaining the immunogenicity such that the material is effective as a vaccine. Typically, formalin, 37% formaldehyde solution, is diluted in from about 1,000 to about 10,000 parts of the antigen preparation and stirred at from about 4° C. to about 60° C. for about 2 hours to about 30 days, preferably the formalin is diluted in from about 2,000 to about 6,000 parts of the virus preparation at from about 20° C. to about 45° C. for from about 2 days to about 6 days, most preferably at about 37° C. for about 3 days.

The vaccine of the present invention may be used to immunize against hepatitis A virus in susceptible mamalian species such as, e.g. marmosets and chimpanzees.

The following examples illustrate the present invention without, however, limiting the same thereto.

EXAMPLE 1

Serial Passage of Hepatitis A Virus in Marmosets to Produce a Viral Strain Suitable for in vitro Cultivation Human hepatitis A virus, strain CR326, is transmitted into a group of 6 Saguinus mystax marmosets by intravenous inoculation of blood from an acutely ill human hepatitis A patient following the procedure of Mascoli et al., P.S.E.B.M. 142: 276-282, 1973.

These inoculated marmosets develop elevations of serum isocitric dehydrogenase (ICD) enzyme values within 30 to 50 days post-inoculation, as well as liver histologic changes consistent with viral hepatitis.

A second passage of the CR326 agent is carried out in mystax marmosets by intravenous inoculation of serum taken from animals of the first passage during the period of ICD elevation into a second group of mystax marmosets. This process induces ICD elevations and liver changes as above.

Third, fourth, and fifth passages of CR326 agent in mystax marmosets are similarly carried out. Extensive serum neutralization assays are carried out to prove that the CR326 agent as propagated in marmosets is in fact the human hepatitis A virus following the procedure of Provost et al., P.S.E.B.M. 142, 1257–1267, 1973.

At the fifth passage level, liver tissue is harvested from an infected mystax marmoset at the time of first onset of serum ICD elevation.

(6) A 1:1,500 dilution of the homogenized liver is used to transmit the CR326 infection to *S. labiatus* (rufiventer) marmosets by intravenous inoculation. This constitutes the sixth serial passage in marmosets and the first passage in rufiventer marmosets. Liver tissue is harvested at the time of ICD elevation onset following the procedure of Provost et al., P.S.E.B.M. 155, 283–286, 1977.

(7) A 1:100 dilution of the homogenized liver is used to carry out a second serial passage of the CR326 agent in a group of 24 rufiventer marmosets. Liver of these animals is harvested as above.

(8) A total of 26 serial passages of the CR326 agent is carried out in rufiventer marmosets by repetition of liver harvest, homogenization, dilution, and intravenous injection.

(9) Thus overall the CR326 agent is serially passed 5 times in mystax marmosets and an additional 26 times in rufiventer marmosets as described in steps 1–8.

(10) Liver tissue from infected rufiventer marmosets at the twenty-fourth to thirty-first marmoset passage level is homogenized and clarified. This homogenized and clarified liver tissue product serves as the inoculum for in vitro cultivation of the hepatitis A virus.

EXAMPLE 2

Growth of Hepatitis A Virus in Marmoset Liver Cell Cultures (1) A rufiventer marmoset is inoculated intravenously with 1 ml of a 1:100 dilution of homogenized, clarified, infected liver tissue in the form of an aqueous extract, prepared as in Example 1

(2) At 24 to 48 hours post-inoculation, prior to disease onset, a portion of the liver of the animal is surgically removed.

(3) The liver tissue is finely minced by chopping on a plastic surface with single edge razor blades. The pieces are thoroughly washed with cell culture medium containing 20 percent fetal calf serum. The washed pieces are deposited on plastic or glass culture vessels and fed three times per week with a culture medium containing Williams medium E plus 20% normal marmoset serum plus $10^{-6}$ molar glucagon plus glutamine, penicillin and streptomycin in the usually used quantities. Dexamethasone, 9-fluoro-11$\beta$,17,21-trihydroxy-16$\alpha$-methylpregna-1,4-diene-3,20-dione and insulin optionally may be present at a concentration of about $10^{-6}$ molar. The medium is used in thin layers; e.g., 2 ml per 25 cm$^2$ culture flask. Incubation is at 35° C. on a rocker platform to give maximum aeration. The gas atmosphere consists of 5% carbon dioxide in air.

(4) Within 7 days a vigorous outgrowth of hepatocyte-like, epithelial cells begins. This outgrowth of large islands of hepatocyte-like cells from the tissue pieces continues slowly over several weeks. Cultures can be maintained for many additional weeks. Hepatocyte function is identified by detection of albumen production and the production of tyrosine amino transferase.

(5) The description of marmoset liver cell cultures in steps 3 and 4 is pertinent whether the liver is obtained from hepatitis A-inoculated or from normal marmosets.

(6) Hepatitis A viral antigen is detected in the cultures prepared from virus inoculated animals beginning at about 7 days post-planting. Such detection is enabled by application of fluorescein-labeled human globulin prepared from hepatitis A convalescent human sera to acetone-fixed coverslip cultures. These preparations are examined in a vertical fluorescence Zeiss microscope with a 63X planapochromat objective and 10X eyepieces.

(7) Hepatitis A viral antigen is detected as brilliant green fluorescent granules located in the cell cytoplasm of hepatocyte-like cells. Both the numbers of granules and their size increase through the period of about 10 weeks post-planting. Heavy levels of the antigen persist through at least 16 weeks post-planting.

(8) The relationship of the granules to hepatitis A virus is proven by the facts that (a) liver cultures prepared from normal marmosets and not exposed to the virus never show development of the granular fluorescence and (b) the granular fluorescence is specifically blocked by pre-application to the fixed preparations of convalescent human hepatitis A sera but not by pre-illness sera from the same patients.

(9) That these liver cultures provide in vitro multiplication of hepatitis A virus is also shown by: (a) at 4 weeks after establishment of the cultures, both supernatant fluids and cell culture extracts produce hepatitis A infection on intravenous inoculation into rufiventer marmosets (b) at 3 weeks and later time periods, typical hepatitis A viral particles, having the properties described by Provost et al., P.S.E.B.M. 148, 532–593, 1975, can be demonstrated in culture extracts by immune electron microscopy, and (c) at 3 weeks and later time periods, hepatitis A viral antigen is detectable by immune adherence hemagglutination culture extracts following the procedure of Miller et al., P.S.E.B.M., 149, 254–261, 1975.

EXAMPLE 3

Growth and Serial Passage of Hepatitis A Virus in Marmoset Liver Cell Cultures Inoculated in vitro (1) Liver tissue surgically removed from a normal rufiventer marmoset is minced and cell cultures are prepared by method as used for infected liver tissue in Example 2.

(2) At about 7 days post-planting, when outgrowth of hepatocytes has begun, the cultures in 25 cm$^2$ flasks are inoculated with hepatitis A virus in the form of 0.1 ml of a 4% aqueous extract of infected marmoset liver derived as in Example 1.

(3) The virus-inoculated liver cell cultures, as well as control uninoculated cultures, are incubated at 35° C. and refed three times per week, as in Example 2.

(4) Glass coverslips are removed, acetone-fixed, stained with fluorescein-labeled hepatitis A antibody-containing globulin, and examined by fluorescence microscopy as given in Example 2.

(5) Hepatitis A viral antigen is detected in virus-inoculated but not in control cultures beginning about 7 days post-inoculation and increasing over a three-week period through 28 days. As in Example 2, the antigen is visible as brilliant green fluorescent cytoplasmic granules. Specificity is proven as in Example 2.

(6) Cells and fluids from both control and virus-inoculated cultures are harvested at 3 to 4 weeks post-inoculation by freezing and thawing the cultures three times. The mixture of broken cells and culture fluid is clarified by low speed centrifugation.

(7) Such culture harvest is additionally shown to contain hepatitis A virus by (a) intravenous inoculation and successful infection of marmosets, (b) electron microscopy and (c) immune adherence hemagglutination, as in Example 2. In all cases, harvests of control cultures are negative for hepatitis A virus activity.

(8) A second in vitro passage of the virus in liver cell culture is made by inoculation of 0.2 ml of the harvest from passage 1 (step 6 above) into new cell cultures in 25 cm$^2$ flasks prepared from normal marmoset liver. A pattern of viral growth and detection is obtained very similar to that outlined in steps 5 to 7.

(9) Such serial in vitro passage of the virus in marmoset liver cultures is carried out five times, and may be carried out indefinitely. With increased passage, better adaptation of the virus to in vitro growth is evidenced by more rapid appearance of large quantitites of cytoplasmic fluorescent granules.

(10) An additional criterion is also used to prove that the agent propagated in this cell culture system is in fact human hepatitis A virus. The harvest from the fourth serial passage is reacted with pre-illness and convalescent sera of human hepatitis A patients prior to inoculation of cell cultures. In all cases the virus is neutralized, i.e., does not transmit infection to the cell culture, by the convalescent sera but not by the pre-illness sera.

EXAMPLE 4

Growth and Serial Passage of Hepatitis A Virus in Primary African Green Monkey Kidney Cell Cultures (1) Kidneys are removed surgically from hepatitis A antibody-free African green monkeys. By standard technology the kidneys are minced and trypsinized, and monolayer cell cultures are prepared.

(2) The cell cultures grow to near confluency within 5–7 days on a medium consisting of Eagle minimal essential medium containing 10% fetal calf serum.

(3) At near confluency the culture medium is replaced with the same medium but with only 0.5% fetal calf serum. Each 25 cm$^2$ flask culture containing 5 ml medium is inoculated with 0.2 ml of a 4% aqueous extract of marmoset liver derived as in Example 1.

(4) The cultures are incubated at 35° C. and refed once per week. Glass coverslips are removed, fixed, and examined by immunofluorescence as in Example 2, at periodic intervals.

(5) Hepatitis A viral antigen is thus detected in virus-inoculated, but not in uninoculated control cultures, beginning about 7 days post-inoculation and increasing over a three-week period through 28 days. As in Examples 2 and 3, the antigen is visible as brilliant green fluorescent cytoplasmic granules. Specificity is proven as in Examples 2 and 3.

(6) Cell cultures are harvested as in Example 3.

(7) The presence of hepatitis A virus is additionally shown to be present in cell culture harvests by (a) inoculation of marmosets, with disease production (b) immune electron microscopy and (c) immune adherence hemagglutination as in Examples 2 and 3. In all cases, harvests made from uninoculated control cultures are free of hepatitis A virus.

(8) Serial in vitro passage of hepatitis A virus in primary green monkey kidney cell cultures is carried out in the same manner as described for marmoset liver cultures in Example 3. Such serial passage can be carried out indefinitely.

EXAMPLE 5

Growth and Serial Passage of Hepatitis A Virus in Other Cell Cultures (1) Using methods as in Example 4 it is found that hepatitis A virus can also be grown and serially passed in cell cultures of the following types: (a) fetal rhesus monkey kidney cell line (FRhK-6), (b) primary chick embryo cell cultures, and (c) fetal rufiventer marmoset kidney cell line. Success in all of these cultures is based on inoculation of the cultures with hepatitis A virus derived as in Example 1.

(2) Hepatitis A virus is serially passed 5 times in FRhK-6 cell line as above. The virus harvest obtained at the fifth passage level is found to successfully infect human diploid lung fibroblast cell cultures, based on criteria as in Examples 2, 3 and 4. The hepatitis A virus infection subsequently can be serially passed in the human diploid line.

(3) Hepatitis A virus is serially passed 5 times in FRhK-6 cell line as in (1). The virus harvest obtained at the fifth passage level is found to successfully infect fetal diploid rhesus monkey lung (FRhL-2) cell cultures, based on criteria as in Examples 2, 3 and 4. The hepatitis A virus infection can subsequently be serially passed in the rhesus diploid line.

EXAMPLE 6

Preparation of Tissue Culture-Grown, Live, Attenuated Hepatitis A Viral Vaccine (1) Hepatitis A virus derived as in Example 1 is serially passed in vitro in primary African green monkey kidney cell cultures as given in Example 4. Cell culture harvests of the virus at passage levels 5 and higher are shown to induce hepatitis A antibody on intravenous inoculation into rufiventer marmosets at a level of 1000 fifty percent tissue culture infective doses as prepared by dilution of the harvest in physiologic saline, but not to produce overt disease in the animals as measured by serum isocitric dehydrogenase valves (none exceeded 1500 Sigma units) and the liver histopathology (only minor changes were noted). Those animals in which hepatitis A antibody is induced by the tissue culture grown virus are rendered resistant to infection on challenge with 1000 fifty percent marmoset infectious doses of hepatitis A virus injected intravenously. Thus the tissue culture-passaged hepatitis A virus is so modified in the process as to constitute a live, attenuated hepatitis A viral vaccine.

(2) Hepatitis A virus similarly passaged in vitro in cultures of fetal rhesus kidney cells (FRhK-6) or fetal rhesus diploid lung cells (FRhL-2) or primary chick embryo cells or human diploid lung fibroblast cells (MRC5, WI-38) or fetal rufiventer marmoset kidney cell line is comparably attenuated after 5 or more serial passages and usable as a live, attenuated vaccine.

EXAMPLE 7

Preparation of Tissue Culture-Grown, Formalin-Inactivated Hepatitis A Viral Vaccine (1) Hepatitis A virus derived as in Examples 1 and 6 is carried through 5 serial in vitro cell culture passages in primary monkey kidney cells as in Examples 4 and 5.

(2) At the fifth passage level, or at higher passage levels, the cell cultures are harvested after 3 weeks incubation at 35° C. or at such time as hepatitis A viral antigen content of the homogenized culture attains a level of 8 or greater units as measured by immune adherence hemagglutination.

(3) Cell culture harvest are obtained by freeze-thawing the entire cultures two times, sloughing off the cell sheets into the culture fluid, and homogenizing the entire mixture by exposure to high intensity sonication for 15 seconds.

(4) The product is clarified by low speed centrifugation, heated at 60° C. for one-half hour and recentrifuged at low speed to further clarify the fluid.

(5) The fluid is then flitered through 0.45 micron veal infusion-treated Millipore filters. This product is treated with 1:4000 formalin for 4 days at 35° C. with continuous agitation. The formalin is partially neutralized at the end of this treatment with sodium bisulphite to leave a residual formalin content of 10 μg/ml of product.

(6) The product is adjusted with phosphate buffered saline to contain $10^{10}$ 27 nm hepatitis A virus particles per ml and stored at 4° C.

(7) The product is free of infectious hepatitis A virus when tested by intravenous inoculation in rufiventer marmosets.

(8) The product is potent as a hepatitis A viral vaccine in that 1 or more 1 ml subcutaneous injections into rufiventer marmosets induce the production of detectable hepatitis A antibody and the animals are rendered immune to challenge with 1000 fifty percent marmoset infectious doses of hepatitis A virus.

(9) Hepatitis A virus similarly treated except carried through 5 serial in vitro cell culture passages in step 1 in fetal rhesus kidney cell line (FRhK-6) or in primary chick embryo cells or in human diploid lung fibroblast cells (MRC5 or WI-38) or in fetal rhesus diploid lung fibroblasts (FRhL-2) produces a similar product free of infectious hepatitis A virus but potent as a hepatitis A viral vaccine.

What is claimed is:

1. A method of growing hepatitis A virus in cell culture comprising modification of the virus by carrying out at least one passage of the virus in a susceptible sub-human primate, removing the infected liver, inoculating an in vitro cell culture with the infected liver, incubating the cell culture until hepatitis A antigen is detectable in the culture cells or fluid, and carrying out at least one additional in vitro passage of the virus in cell culture.

2. A method according to claim 1 wherein the sub-human primate is a marmoset monkey, an owl monkey, a rhesus monkey, an African green monkey, a cynomolgus monkey, or a chimpanzee.

3. A method according to claim 2 wherein the marmoset monkey is *Saguinus mystax* or *S. labiatus* (rufiventer).

4. A method according to claim 1 wherein at least 5 passages of hepatitis A virus are carried out in sub-human primates.

5. A method according to claim 1 wherein the virus is passaged at least twice in each of two different species of susceptible sub-human primates.

6. A method according to claim 1 wherein the cell cultures consist of primary, continuously cultivated, or transformed cells derived from primate liver or kidney.

7. A method according to claim 1 wherein the hepatitis A virus is serially passaged at least 5 times in a cell culture suitable for human vaccine use, the cell culture being selected from human diploid lung fibroblasts, primary African green monkey kidney cells, primary chick embryo fibroblasts, or fetal rhesus diploid lung cells.

8. A live attenuated hepatitis A virus vaccine comprising an antigenic and immunogenic hepatitis A virus which has been modified by at least one passage in the liver of a sub-human primate susceptible to hepatitis A virus disease and by at least two serial in vitro passages in cell culture.

9. The hepatitis A virus vaccine according to claim 8 in which the virus has been inactivated by contact with an agent effective to inactivate the virus.

* * * * *